(12) United States Patent
Ohmura et al.

(10) Patent No.: US 9,429,941 B2
(45) Date of Patent: Aug. 30, 2016

(54) CONTROL APPARATUS OF VEHICLE

(71) Applicant: HONDA MOTOR CO., LTD., Minato-ku, Tokyo (JP)

(72) Inventors: Shigeru Ohmura, Wako (JP); Kei Oshida, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 3 days.

(21) Appl. No.: 14/547,701

(22) Filed: Nov. 19, 2014

(65) Prior Publication Data

US 2015/0153733 A1 Jun. 4, 2015

(30) Foreign Application Priority Data

Dec. 3, 2013 (JP) .................................. 2013-250030

(51) Int. Cl.
*G05D 1/00* (2006.01)
*G05D 1/02* (2006.01)
*B60K 28/06* (2006.01)
(Continued)

(52) U.S. Cl.
CPC ............. *G05D 1/0061* (2013.01); *B60K 28/06* (2013.01); *B60K 28/066* (2013.01); *B60W 30/165* (2013.01); *B60W 30/17* (2013.01); *G05D 1/0295* (2013.01); *G08G 1/20* (2013.01); *G08G 1/22* (2013.01); *A61B 5/18* (2013.01); *B60W 2040/0827* (2013.01);
(Continued)

(58) Field of Classification Search
CPC ............. G05D 1/0061; G05D 1/0295; G05D 2201/0213; B60K 28/06; B60K 28/066; B60W 30/165; B60W 30/17; B60W 2040/0827; B60W 2040/0836; B60W 2040/0845; B60W 2540/26; A61B 5/18; G08G 1/20; G08G 1/22

See application file for complete search history.

(56) References Cited

U.S. PATENT DOCUMENTS 6,141,619 A * 10/2000 Sekine ............... B60K 31/0058
340/990
6,292,737 B1 * 9/2001 Higashimata ...... B60K 31/0008
180/167

(Continued)

FOREIGN PATENT DOCUMENTS

DE        103 48 635 A1    5/2005
DE   10 2006 039 682 A1    2/2008

(Continued)

OTHER PUBLICATIONS

Office Action, dated Aug. 13, 2015, issued in the corresponding German Patent Application 10 2014 224 645.8 with the English translation thereof.

(Continued)

*Primary Examiner* — Russell Frejd (74) *Attorney, Agent, or Firm* — Carrier Blackman & Associates, P.C.; Joseph P. Carrier; William D. Blackman (57) ABSTRACT

A control apparatus of a vehicle is provided. In the control apparatus, an unable-to-drive state of the driver of the vehicle is detected or determined. The unable-to-drive state is a state where the driver is unable to drive the vehicle. When the emergency that the driver has become the unable-to-drive state is detected or determined, the detection or determination result is notified to the outside. A leading vehicle which is adapted to leading the vehicle based on the notification, is recognized. Automatic follow-up running control is performed wherein the vehicle is made to automatically follow the leading vehicle.

6 Claims, 9 Drawing Sheets

(51) Int. Cl.
*B60W 30/16* (2012.01)
*B60W 30/165* (2012.01)
*B60W 30/17* (2012.01)
*B60W 40/08* (2012.01)
*A61B 5/18* (2006.01)
*G08G 1/00* (2006.01)

(52) U.S. Cl.
CPC .............. *B60W 2040/0836* (2013.01); *B60W 2040/0845* (2013.01); *B60W 2540/26* (2013.01); *G05D 2201/0213* (2013.01)

(56) References Cited

U.S. PATENT DOCUMENTS

| | | | | |
|---|---|---|---|---|
| 7,280,903 B2* | 10/2007 | Arai | ...................... | B60W 30/16 340/435 |
| 7,337,056 B2* | 2/2008 | Arai | .................. | B60K 31/0008 180/170 |
| 7,663,502 B2* | 2/2010 | Breed | ...................... | B60C 11/24 340/12.25 |
| 8,050,863 B2* | 11/2011 | Trepagnier | ............ | B60W 30/00 180/167 |
| 8,346,480 B2* | 1/2013 | Trepagnier | ............ | B60W 30/00 180/167 |
| 2007/0182529 A1* | 8/2007 | Dobler | .................. | B60K 28/06 340/438 |
| 2010/0030434 A1 | 2/2010 | Okabe et al. | | |
| 2013/0041576 A1* | 2/2013 | Switkes | ................. | G08G 1/166 701/123 |
| 2013/0066511 A1* | 3/2013 | Switkes | ................. | G08G 1/166 701/28 |
| 2013/0131098 A1* | 5/2013 | Clarke | ................... | A61K 9/006 514/284 |
| 2013/0179024 A1* | 7/2013 | Nordbruch | ............... | A61B 5/18 701/23 |
| 2013/0226408 A1* | 8/2013 | Fung | ..................... | B60W 40/09 701/41 |
| 2013/0245886 A1* | 9/2013 | Fung | ..................... | B60K 28/06 701/36 |

FOREIGN PATENT DOCUMENTS

| | | |
|---|---|---|
| DE | 10 2011 109 618 A1 | 2/2013 |
| DE | 10 2012 008 090 A1 | 10/2013 |
| JP | 2001219760 A * | 8/2001 |
| JP | 2003157493 A * | 5/2003 |
| JP | 2007293625 A * | 11/2007 |
| JP | 2009-037415 A | 2/2009 |
| JP | 2009-151522 A | 7/2009 |
| JP | 2010036656 A * | 2/2010 |
| JP | 2010-125923 A | 6/2010 |
| JP | 2012230523 A * | 11/2012 |

OTHER PUBLICATIONS

Office Action issued on Mar. 1, 2016 to the corresponding Japanese Patent Application 2013-250030.

Office Action issued Jul. 12, 2016 in the corresponding Japanese Patent Application 2013-250030.

* cited by examiner

CONTROL APPARATUS OF VEHICLE

BACKGROUND OF THE INVENTION

1. Field of the Invention

The present invention relates to a control apparatus of a vehicle, for stopping an unable-to-drive vehicle at an appropriate position, the unable-to-drive vehicle being a vehicle of which the driver has become an unable-to-drive state where the driver is unable to drive the vehicle, due to, for example, a heart attack or a cerebral infarction.

2. Description of the Related Art

Japanese patent laid-open publication No. 2010-125923 discloses a vehicle control apparatus for stopping a vehicle at an appropriate position when the driver has become the unable-to-drive state. According to this apparatus, the stop position of the vehicle is decided according to the road configuration when the driver has become unable to drive the vehicle, automatic driving of the vehicle is performed to the decided position, and the vehicle is stopped at the position. For example, when the vehicle runs on a left-curved one-lane road with no opposite lane, the control of stopping the vehicle on the right side of the road, which hardly becomes a blind spot, is performed.

According to the above conventional apparatus, it is possible to stop the vehicle at an appropriate position when the driver has become the unable-to-drive state. However, for promptly performing the life saving activity for the driver, it is not sufficient to simply stop the vehicle.

SUMMARY OF THE INVENTION

The present invention was made contemplating the above-described point, and an objective of the present invention is to provide a control apparatus of a vehicle, which makes it possible to prevent wild running of the vehicle when the driver has become the unable-to-drive state, and to promptly perform the life saving activity for the driver.

To attain the above objective, the present invention provides a control apparatus of a vehicle (1, VE), comprising detection/determination means, notifying means, leading vehicle recognizing means, and follow-up running control means. The detection/determination means detects or determines an unable-to-drive state of the driver of the vehicle, the unable-to-drive state being a state where the driver is unable to drive the vehicle. The notifying means notifies the outside (VC, SVR) of the detection/determination result by the detection/determination means when the detection/determination means detects or determines that the driver has become the unable-to-drive state. The leading vehicle recognizing means recognizes a leading vehicle (VR) which is adapted to leading the vehicle (VE) based on the notification made by the notifying means. The follow-up running control means makes the vehicle (VE) automatically follow the leading vehicle (VR).

With this configuration, when it is detected or determined that the driver has become the unable-to-drive state, the detection/determination result is notified to the outside. The leading vehicle which is adapted to leading the present vehicle (unable-to-drive vehicle) based on the notification, is recognized by, for example, the communication between the present vehicle and the leading vehicle, and the control of making the present vehicle automatically follow the leading vehicle is performed. Accordingly, the emergency that the driver of the present vehicle has become the unable-to-drive state is notified, for example, to another vehicle or a server which is able to communicate with the present vehicle. The other vehicle which exists near the present vehicle and has received the notification, can lead the present vehicle to guide it, for example, to a medical institution. Consequently, it is possible to prevent wild running of the vehicle, and to promptly perform the life-saving activity of the driver.

Preferably, the control apparatus further comprises invalidating means for invalidating an operation system which is operated by the driver of the vehicle (VE).

With this configuration, the operation system of the vehicle of which the driver has become the unable-to-drive state is invalidated. Accordingly, even if the steering wheel or the accelerator pedal is erroneously moved by the driver's collapse, the vehicle can continue the automatic follow-up running without influence of the erroneous operation.

Preferably, the control apparatus further comprises joining point obtaining means and automatic joining driving means, wherein the joining point obtaining means obtains a joining point (PJN) at which the vehicle (VE) joins the leading vehicle (VR), and the automatic joining driving means performs autonomous and automatic driving of the vehicle (VE) to the joining point (PJN).

In this specification, the "autonomous and automatic driving" does not mean the automatic driving wherein the vehicle is made to automatically follow another vehicle running immediately ahead of the vehicle, but means the driving wherein the vehicle is made to automatically run along the lane border line (white lines with intervals) on a road, the guard rails installed on the road side, or the like with monitoring obstacles existing ahead of the vehicle using a radar and a camera.

With this configuration, the joining point at which the present vehicle joins the leading vehicle is obtained, and autonomous and automatic driving of the present vehicle is performed to the joining point. If the leading vehicle or the server decides the joining point and the joining point information is transmitted, the present vehicle receives the transmission to obtain the joining point information. Driving of the present vehicle is performed to the joining point by the autonomous and automatic driving of a comparatively low speed with keeping the same running lane. Consequently, the present vehicle can be made to automatically join the leading vehicle.

The present invention provides another control apparatus of a vehicle (V1, VR) comprising unable-to-drive vehicle recognizing means and lead running control means. The unable-to-drive vehicle recognizing means recognizes an unable-to-drive vehicle (VE) of which the driver has become an unable-to-drive state where the driver is unable to drive the vehicle (VE). The lead running control means performs a lead running control for making the unable-to-drive vehicle (VE) follow the vehicle (V1, VR).

With this configuration, the unable-to-drive vehicle of which the driver has become the unable-to-drive state is recognized, for example, by the communication between the vehicles, or the notice from the server, and the lead running control for making the unable-to-drive vehicle follow the present vehicle (leading vehicle), is performed. Accordingly, it is possible to prevent wild running of the unable-to-drive vehicle, and to lead the unable-to-drive vehicle to a comparatively safe place such as a road side zone for emergency stoppage of vehicles, or to a medical institution.

Preferably, the control apparatus further comprises invalidating means for invalidating an operation system which is operated by the driver of the unable-to-drive vehicle (VE).

With this configuration, the operation system of the vehicle of which the driver has become the unable-to-drive state is invalidated. Accordingly, even if the steering wheel or the accelerator pedal is erroneously moved by the driver's collapse, the lead running control for making the unable-to-drive vehicle follow the present vehicle can be continued without influence of the erroneous operation.

Preferably, the control apparatus further comprises joining point obtaining means and automatic joining driving means. The joining point obtaining means obtains a joining point (PJN) at which the vehicle (VR) joins the unable-to-drive vehicle (VE). The automatic joining driving means autonomously and automatically drives the vehicle (VR) to the joining point (PJN).

With this configuration, the joining point at which the present vehicle joins the unable-to-drive vehicle is obtained, and the autonomous and automatic driving of the present vehicle is performed to the joining point. If the joining point is decided by the present vehicle, or the joining point decided by the server is notified, the running of the present vehicle is performed to the joining point by the autonomous and automatic driving of a comparatively low speed with keeping the same running lane. Accordingly, it is possible to make the present vehicle automatically join the unable-to-drive vehicle.

Preferably, the control apparatus further comprises final stop position obtaining means for obtaining a final stop position (PDST) at which the unable-to-drive vehicle (VE) should be stopped, wherein the lead running control means leads the unable-to-drive vehicle (VE) to the final stop position (PDST) by autonomous and automatic driving.

With this configuration, the final stop position at which the unable-to-drive vehicle should be stopped is obtained, and the lead running control for leading the unable-to-drive vehicle to the final stop position by the autonomous and automatic driving, is performed. The final stop position is, for example, a safe road side zone or a position near a medical institution, which is determined in the present vehicle or notified from the server. Accordingly, the present vehicle can safely lead the unable-to-drive vehicle to the final stop position and stop it there without any load on the driver of the present vehicle.

Preferably, the final stop position (PDST) is determined based on a configuration of the road on which the vehicle (VR) is running.

With this configuration, the final stop position is determined based on a configuration of the road on which the present vehicle is running. Accordingly, stoppage at a curved location, for example, is avoided, and the unable-to-drive vehicle can be stopped on the straight road of a long distance view or at a position near which a space for stoppage exists on the road shoulder, thereby enhancing safety of the vehicles.

Alternatively, the final stop position (PDST) is determined based on location information of medical institutions.

With this configuration, the final stop position is determined based on location information of medical institutions. Accordingly, it is possible to stop the unable-to-drive vehicle near a medical institution and to promptly perform the life-saving activity for the driver of the unable-to-drive vehicle.

DETAILED DESCRIPTION OF THE PREFERRED EMBODIMENTS

Preferred embodiments of the present invention will now be described with reference to the drawings.

First Embodiment

Figure 1:
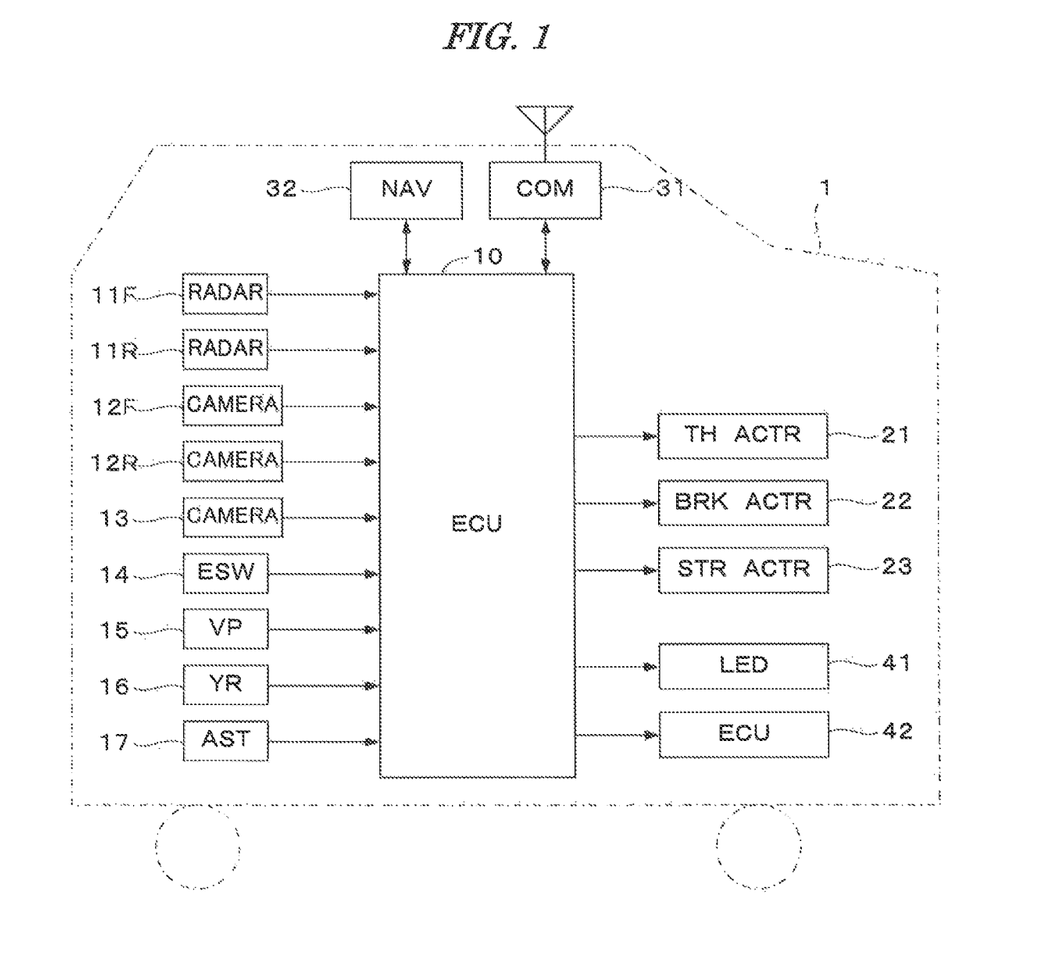
FIG. 1 is a block diagram showing a configuration of a control apparatus of a vehicle according to one embodiment of the present invention.

FIG. 1 is a block diagram showing a configuration of a control apparatus of a vehicle according to one embodiment of a present invention. This control apparatus is mounted on a vehicle 1, and the control apparatus is provided with an electronic control unit (hereinafter referred to as "ECU") 10, radars 11F and 11R connected to the ECU 10, cameras 12F, 12R, and 13, an emergency switch 14, a vehicle speed sensor 15, a yaw-rate sensor 16, a steering angle sensor 17, a communication unit 31, a navigation unit 32, a throttle actuator 21, a brake actuator 22, and a steering actuator 23. The cameras 12F and 12R respectively obtain images of a forward view and a backward view of the vehicle 1. The camera 13 obtains an image of a head of the driver of the vehicle 1. The emergency switch 14 is provided for the driver to turn on upon an emergency, such that the driver is going to be unconscious by a heart attack or the like. The vehicle speed sensor 15 detects a vehicle speed (running speed) of the vehicle 1. The yaw-rate sensor 16 detects a yaw-rate of the vehicle 1 (an angular velocity of rotation around the vertical axis passing the center of gravity of the vehicle 1). The steering angle sensor 17 detects a steering angle AST of a steering wheel of the vehicle 1. The throttle actuator 21 actuates a throttle valve of an internal combustion engine for driving the vehicle 1. The brake actuator 22 actuates brakes of the vehicle 1, and the steering actuator 23 actuates a steering shaft of the vehicle 1.

An LED display 41 and another ECU 42 are further connected to the ECU 10. The LED display 41 is provided for notifying the driver of performing the autonomous and automatic driving, when the autonomous and automatic driving of the vehicle 1 is performed. The ECU 42 controls the internal combustion engine and a transmission for driving the vehicle 1. Preferably, the vehicle 1 is provided with reflectors for the radar waves, which are mounted on the rear and front portions of the vehicle 1.

The radars 11F and 11R are directed respectively forward and backward with respect to the vehicle 1 and mounted at appropriate positions of the vehicle 1. The ECU 10 detects objects existing in front or rear of the vehicle 1, and also detects a distance to the detected object. The cameras 12F and 12R are mounted at appropriate positions for respectively obtaining images of the forward and backward views of the vehicle 1. The ECU 10 determines circumstances of the right and left front sides and the right and left rear sides of the vehicle 1 by analyzing the images obtained by the cameras 12F and 12R. Further, the ECU 10 detects the running direction of the vehicle 1 with the yaw-rate YR detected by the yaw-rate sensor 16.

The ECU 10 detects, for example, motions and viewing directions of eye balls of the driver based on the images obtained by the camera 13, and determines the unable-to-drive state of the driver according to the detected result. When it is determined based on the images obtain by the camera 13 that the driver has become the unable-to-drive state, or when the emergency switch 14 is turned on, the ECU 10 performs an emergency coping control, to transmit emergency information to other vehicles which exist in the vicinity of the vehicle 1 and are provided with the control apparatus having the same functions as the functions of the control apparatus of the vehicle 1 shown in FIG. 1.

Thereafter, the control for stopping the vehicle 1 at a comparatively safe place or a place near a medical institution is performed with a convoy follow-up running wherein the vehicle 1 follows immediately after another vehicle (hereinafter referred to as "leading vehicle") which joins the vehicle 1 according to the emergency information transmitted by the ECU 10. The convoy follow-up running can be performed by applying a convoy running control method which is already known. Specifically, the convoy follow-up running is performed by detecting a distance between the vehicle 1 and the leading vehicle using the radar 11F, and obtaining necessary information with the communication between the vehicle 1 and the leading vehicle. The vehicle of which the driver has become the unable-to-drive state will be hereinafter referred to as "unable-to-drive vehicle". In some cases, the vehicle 1 corresponds to the unable-to-drive vehicle VE, and in other cases, the vehicle 1 corresponds to the leading vehicle VR according to the emergency information transmitted from the unable-to-drive vehicle VE.

In the case where the vehicle 1, as the leading vehicle VR, leads the unable-to drive vehicle VE, the ECU 10 decides a joining point PJN at which the vehicle 1 joins the unable-to-drive vehicle VE, and notifies the unable-to-drive vehicle VE of the joining point PJN using the communication unit 31. Running of the vehicle 1 to the joining point PJN is normally performed by the autonomous and automatic driving, and running of the vehicle 1 from the joining point PJN to a final stop position PDST is also performed similarly.

Referring FIGS. 2A-3C, an outline of the controls upon occurrence of the emergency in this embodiment (the emergency coping control in the unable-to-drive vehicle VE, and the emergency leading control in the leading vehicle VR) is described below.

Figure 2A:
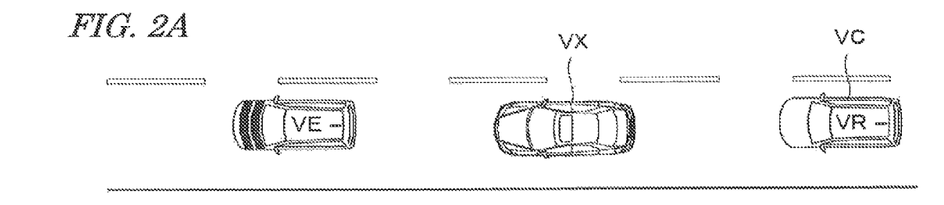
FIGS. 2A-2E and 3A-3C are drawings for illustrating a control upon occurrence of the emergency (first embodiment)

FIG. 2A shows a condition where the emergency has occurred. Specifically, the unable-to-drive vehicle VE runs ahead of the vehicle VC on a two-lane road, and another vehicle VX runs between the two vehicles VE and VC. The vehicle VS is able to communicate with the vehicle VE, but the vehicle VX is unable to communicate with the vehicles VE and VC. The vehicle VX is therefore referred to as "unable-to-communicate vehicle". If the emergency information is transmitted in this condition, the vehicle VC receives the emergency information and becomes the leading vehicle VR. The emergency information includes at least a vehicle identifying information VEID and the present position PTMP of the unable-to-drive vehicle VE, and the emergency occurrence time tEM. The emergency information may further include visible information such as a vehicle model, a body color, a vehicle number of the vehicle VE.

The leading vehicle VR determines a point which is near the present position PTMP of the unable-to-drive vehicle VE and exists ahead in the running direction, as a joining point PJN and transmits a leading vehicle information. The leading vehicle information includes the vehicle identifying information VRID and a joining point information indicative of the joining point PJN.

Figure 2B:
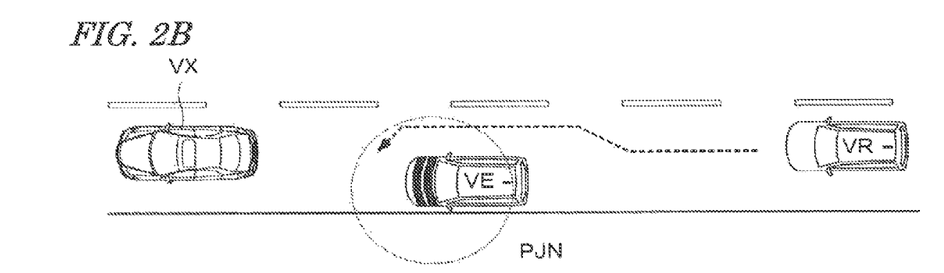
Figure 2C:
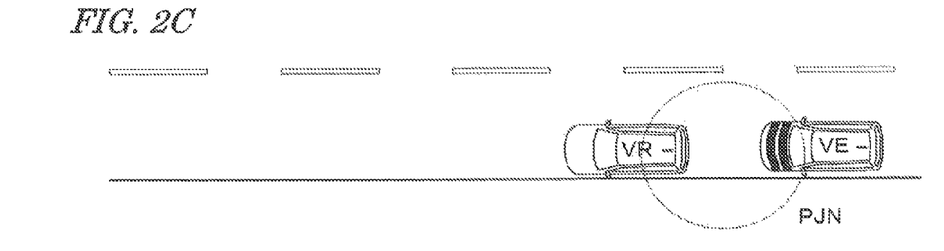

The unable-to-drive vehicle VE runs on the present running road with the autonomous and automatic driving, and stops at the joining point PJN set on the present road as shown in FIG. 2B. The unable-to-communicate vehicle VX runs forward avoiding the unable-to-drive vehicle VE, and the leading vehicle VR, with the autonomous and automatic driving, runs to a position in front of the stopped unable-to-drive vehicle VE, and stops there (FIG. 2C).

Figure 2D:
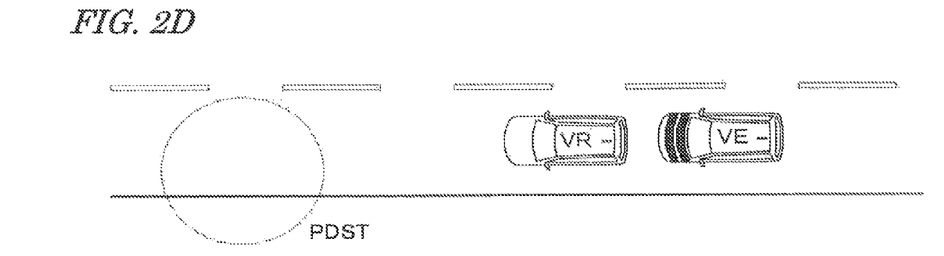
Figure 2E:
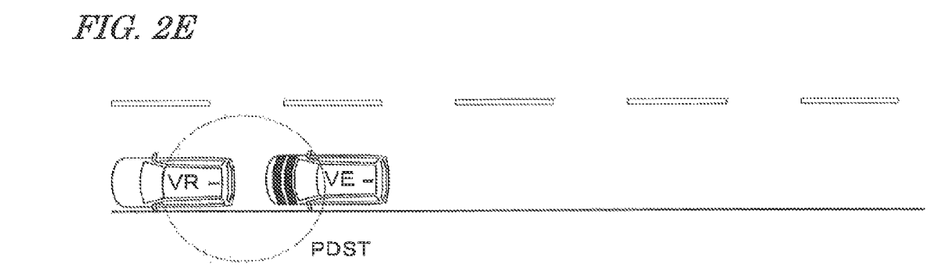

Thereafter, the leading vehicle VR determines a final stop position PDST and begins the convoy lead driving toward the final stop position PDST, at the same time the unable-to-drive vehicle VE begins the convoy follow-up driving (FIG. 2D). The both vehicles VR and VE reach the final stop position PDST to stop there (FIG. 2E). The final stop position PDST is determined based on a configuration of the present road, for example, as a position on the straight road portion of a long distance view, or a position near which the space for stoppage exists on the road shoulder. If a medical institution exists near the vehicles VR and VE, the final stop position PDST is determined as a position near the medical institution.

In the example shown in FIGS. 2A-2E, only one unable-to-communicate vehicle VX exists between the unable-to-drive vehicle VE and the leading vehicle VR. If a plurality of unable-to-communicate vehicles VX exist, the similar emergency control can be applied.

Figure 3A:
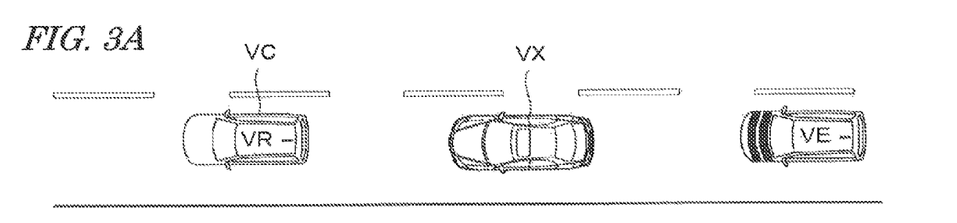

FIG. 3A shows an example where the vehicles VC and VE run in reverse order compared with the example of FIG. 2A. That is, the vehicle VC runs ahead of the unable-to-drive vehicle VE when the emergency has occurred, and the unable-to-communicate vehicle VX exists between the vehicles VC and VE.

Figure 3B:
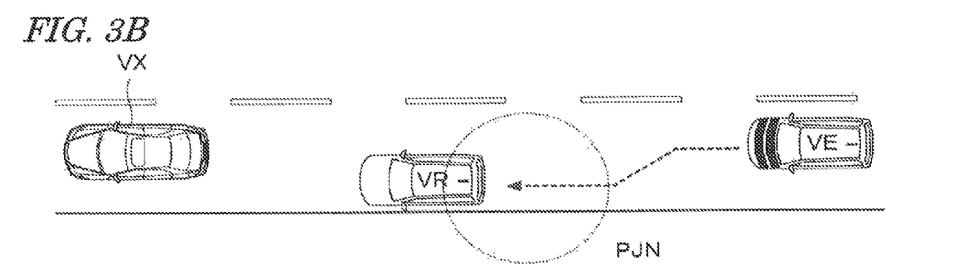
Figure 3C:
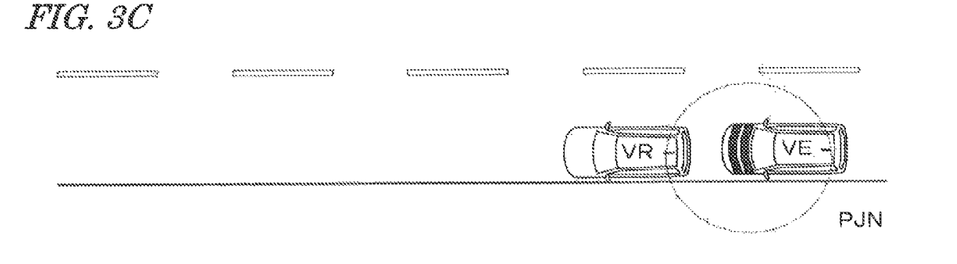

The vehicle VC receives the emergency information, and becomes the leading vehicle VR. The leading vehicle VR determines a place positioned near the present position and ahead in the running direction, as the joining point PJN, and transmits the leading vehicle information. When the leading vehicle VR stops at the joining point PJN, the unable-to-communicate vehicle VX runs avoiding the leading vehicle VR (FIG. 3B). The unable-to-drive vehicle VE runs on the present road with the autonomous and automatic driving, and recognizes the leading vehicle VR with the communication between vehicles, to stop immediately behind the leading vehicle VR as shown in FIG. 3C. Thereafter, the vehicles VR and VE move to the final stop position PDST with the convoy running similarly to the example of FIGS. 2D and 2E.

It is to be noted that the similar emergency control can be applied when a plurality of unable-to-communicate vehicles VX exist between the unable-to-drive vehicle VE and the leading vehicle VR. If there is no unable-to-communicate vehicle VX between the vehicles VE and VR, the vehicles VE and VR immediately begin the convoy running and run forward to the final stop position PDST.

Figure 4:
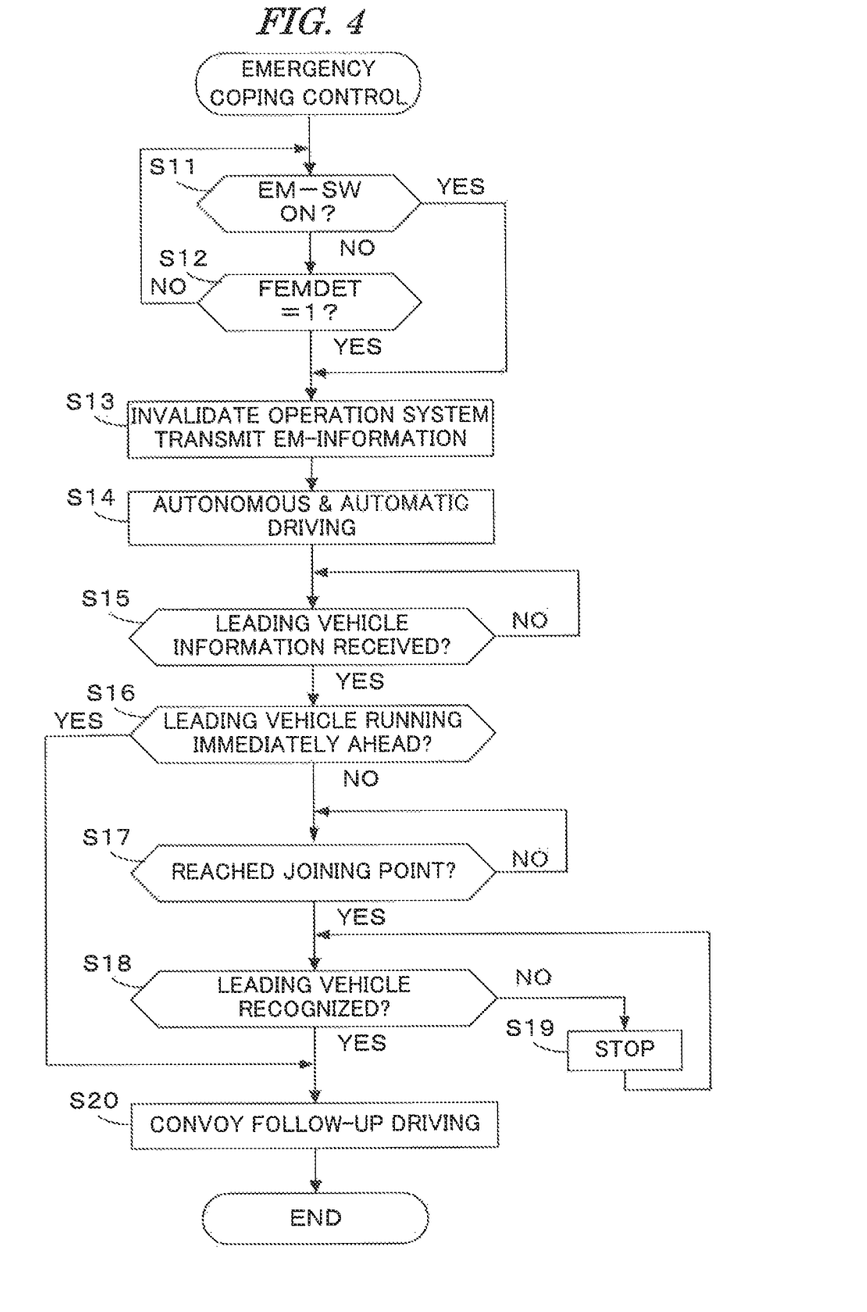
FIG. 4 is a flowchart of a control for coping with the emergency, the control being performed when the driver of the present vehicle has become the unable-to-drive state (first embodiment)

FIG. 4 is a flowchart of the emergency coping control performed when the driver of the vehicle 1 has become the unable-to-drive state.

In step S11, it is determined whether or not the emergency switch (EM-SW) 14 is turned on. If the answer to step S11 is negative (NO), it is determined whether or not an unable-to-drive state detection flag FEMDET is "1" (step S12). The unable-to-drive state detection flag FEMDET is set to "1" when the emergency that the driver of the vehicle 1 has become the unable-to-drive state is determined to be occurred in the process (not shown) for detecting the unable-to-drive state.

If the answer to step S11 or S12 becomes affirmative (YES), the process proceeds to step S13, in which a command for invalidating the operation system (accelerator pedal, brake pedal, steering wheel, and switches) of the vehicle 1 is provided to the ECU 42, the emergency information (EM information) is transmitted. The autonomous and automatic driving is thereafter started wherein the vehicle 1 runs maintaining the present running lane (step S14).

In step S15, it is determined whether or not the leading vehicle information is received. If the leading vehicle information is received, it is further determined whether or not the leading vehicle VR is running immediately ahead of the vehicle 1 (step S16). If the answer to step S16 is affirmative (YES), the process proceeds to step S20, to immediately start the convoy follow-up driving.

If the answer to step S16 is negative (NO), the autonomous and automatic driving is continued toward the specified joining point PJN. In step S17, it is determined whether or not the vehicle 1 has reached the joining point PJN. If the vehicle 1 has reached the joining point PJN, it is determined whether or not the leading vehicle VR has been recognized and reached the position immediately ahead of the vehicle 1 (step S18). If the leading vehicle VR cannot be recognized promptly, the vehicle 1 stops and waits for the leading vehicle VR (step S19).

If the leading vehicle VR is recognized at the position immediately ahead of the vehicle 1, the convoy follow-up driving is started (step S20). Accordingly, the vehicle 1 (the unable-to-drive vehicle VE) stops at the final stop position PDST at which the leading vehicle VR stops.

It is to be noted that emergency stop for promptly stopping the vehicle 1 is performed if the condition that the answer to step S15 is negative (NO) continues for a predetermined time period.

Figure 5:
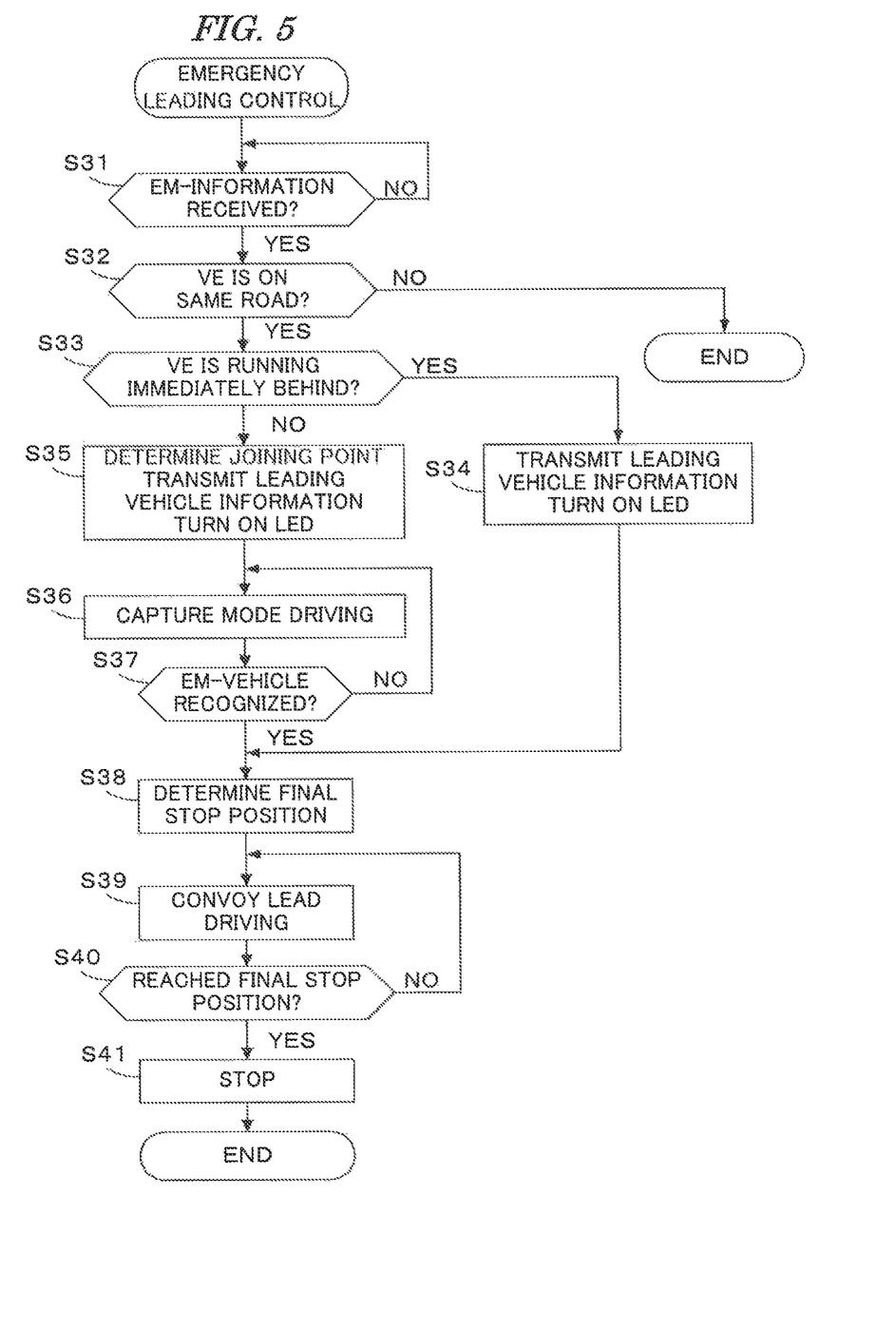
FIG. 5 is a flowchart of an emergency leading control which is performed when the present vehicle corresponds to a vehicle which should lead the unable-to-drive vehicle (first embodiment)

FIG. 5 is a flowchart of the emergency leading control performed when the vehicle 1 is adapted to the leading vehicle VR.

In step S31, it is determined whether or not the emergency information has been received. If the emergency information has been received, the process proceeds to step S32, in which it is determined whether or not the unable-to-drive vehicle VE is on the same road. If the answer to step S32 is negative (NO), the process ends.

If the answer of step S32 is affirmative (YES), it is determined whether or not the unable-to-drive vehicle VE is running immediately behind the vehicle 1 (the leading vehicle VR) (step S33). If the answer to step S33 is affirmative (YES), the leading vehicle information is transmitted, and the LED display 41 is turned on for informing the driver of performing the autonomous and automatic driving (step S34). Thereafter, the process immediately proceeds to step S38.

If the answer to step S33 is negative (NO), the joining point PJN is determined, the leading vehicle information is transmitted, and the LED display 41 is turned on (step S35). Next, a capture mode driving for capturing the unable-to-drive vehicle VE, is started and the vehicle 1 runs toward the joining point PJN (step S36). In step S37, it is determined whether or not the unable-to-drive vehicle (EM vehicle) VE has been recognized immediately behind the vehicle 1 at the joining point PJN. If recognized, the final stop position PDST is determined (step S38).

The determination of the final stop position PDST is made based on the information stored in the navigation unit 32. In step S39, the convoy lead driving is performed. That is, the autonomous and automatic driving is performed to the final stop position PDST with the unable-to-drive vehicle VE being made to automatically follow the vehicle 1. The vehicle 1 stops when reaching the final stop position PDST (steps S40 and S41), and the process ends.

In this embodiment, the position information is obtained by the navigation unit 32, and the image information obtained by the cameras 12F and 12R is referred to during the autonomous and automatic driving, if necessary.

As described above, in this embodiment, when the emergency that the driver of the vehicle 1 has become the unable-to-drive state is detected by the emergency switch 14, or determined based on the image obtained by the camera 13, the emergency is notified of another vehicle VC (VR). The leading vehicle VR, which is adapted to leading the vehicle 1 based on the notification, is recognized with the communication via the communication unit 31, and the control for making the vehicle 1 automatically follow the leading vehicle VR, is performed. Accordingly, the vehicle 1 can safely reach and stop at the final stop position PDST. Consequently, wild running of the vehicle 1 can be prevented, and the life-saving activity of the driver can be performed promptly if a medical institution exists near the final stop position PDST.

Further, the operation system of the vehicle 1 is invalidated upon occurrence of the emergency. Accordingly, even if the steering wheel or the accelerator pedal is erroneously moved by the driver's collapse or the like, the autonomous and automatic driving and the convoy follow-up driving can be continued without influence of the erroneous operation.

The joining point PJN at which the vehicle 1 joins the leading vehicle VR is obtained with the leading vehicle information, and the autonomous and automatic driving of the vehicle 1 is performed to the joining point PJN. Specifically, the running by the autonomous and automatic driving of a comparatively low speed with keeping the same running lane, is performed to the joining point PJN, and the vehicle 1 can automatically be made to join the leading vehicle VR.

Further, when the vehicle 1 receives the emergency information, the unable-to-drive vehicle VE of which the driver has become the unable-to-drive state is recognized, for example, by the communication between the vehicles with the communication unit 31, and the lead running control for making the unable-to-drive vehicle VE follow the vehicle 1 as the leading vehicle VR, is performed. Accordingly, it is possible to prevent wild running of the unable-to-drive vehicle VE, and to lead the unable-to-drive vehicle VE to the final stop position PDST, which is, for example, a comparatively safe place such as the road side zone for emergency stoppage of vehicles, or a place near a medical institution.

Further, the joining point PJN at which the vehicle 1 joins the unable-to-drive vehicle VE is determined, and the autonomous and automatic driving of the vehicle 1 is performed to the joining point PJN. Specifically, the running of the vehicle 1 is performed to the joining point PJN by the autonomous and automatic driving of a comparatively low speed with keeping the same running lane. Accordingly, it is possible to make the vehicle 1 automatically join the unable-to-drive vehicle.

Further, the final stop position PDST at which the unable-to-drive vehicle VE is led to be stopped is determined, and the autonomous and automatic driving is performed to lead the unable-to-drive vehicle VE to the final stop position PDST. Accordingly, it is possible with no load on the driver of the vehicle 1 to lead the unable-to-drive vehicle VE to the final stop position PDST and to stop it there.

Further, since the final stop position PDST is determined based on the road configuration, stoppage at a curved location, for example, is avoided, and the unable-to-drive vehicle VE can be stopped on a straight road of a long distance view or at a position near which the space for stoppage exists on the road shoulder, thereby enhancing safety of the vehicles VE, VR, and other vehicles running nearby.

Alternatively, the final stop position PDST may be determined based on location information of medical institutions. In such case, it is possible to stop the unable-to-drive vehicle VE near a medical institution and to promptly perform the life-saving activity for the driver of the unable-to-drive vehicle VE.

In this embodiment, if the vehicle 1 corresponds to the unable-to-drive vehicle VE, the camera 13 and the emergency switch 14 constitute a part of the detection/determination means, and the communication unit 31 constitutes a part of the notifying means, leading vehicle recognizing means, follow-up running control means, joining point obtaining means, and automatic joining driving means. The radar 11F constitutes a part of the follow-up running control means and automatic joining driving means, and the actuators 21-23 constitute a part of the follow-up running control means and automatic joining driving means. The navigation unit 32 constitutes a part of the joining point obtaining means, and the ECU 10 constitutes a part of the detection/determination means, notifying means, leading vehicle recognizing means, follow-up running control means, joining point obtaining means, and automatic joining driving means. The cameras 12F and 12R may sometimes constitute a part of the automatic joining driving means.

If the vehicle 1 corresponds to the leading vehicle VR, the communication unit 31 constitutes a part of the unable-to-drive vehicle recognizing means, lead running control means, and automatic joining driving means. The radars 11F and 11R constitute a part of the lead running control means and automatic joining driving means, and the actuators 21-23 constitute a part of the lead running control means and automatic joining driving means. The navigation unit 32 constitutes a part of the final stop position obtaining means, and the ECU 10 constitutes a part of the unable-to-drive vehicle recognizing means, lead running control means, joining point obtaining means, automatic joining driving means, and final stop position obtaining means. The cameras 12F and 12R may sometimes constitute a part of the automatic joining driving means and lead running control means.

Modification

In the above-described embodiment, transmission of the emergency information and the leading vehicle information is performed via communication between the unable-to-drive vehicle VE and the leading vehicle VR. The transmission may be performed via an external server (emergency coping center) SVR which is able to communicate with both of the unable-to-drive vehicle VE and the leading vehicle VR. In such case, the emergency information is transmitted to another vehicle VC via the external server SVR, and the notified vehicle VC becomes the leading vehicle VR. Then, the leading vehicle information is transmitted from the leading vehicle VR to the unable-to-drive vehicle VE via the external server SVR.

In this modification, the external server SVR may determine the joining point PJN and the final stop position PDST, and transmit the determined location information to the unable-to-drive vehicle VE and the leading vehicle VR.

Further, the leading vehicle VR may command the unable-to-drive vehicle VE to invalidate the operation system via communication between vehicles. In such case, the ECU 10 and the communication unit 31 of the leading vehicle VR constitute the invalidating means.

Second Embodiment

In this embodiment, if the driver has become the unable-to-drive state, the unable-to-drive vehicle VE is promptly stopped, the stop position PSTP is determined as the joining point PJN, and the leading vehicle VR runs toward the joining point PJN. Further, in the above-described first embodiment, only when the vehicle VC having the same control apparatus as that of the vehicle VE runs on the same road on which the vehicle VE runs, the vehicle VC is adapted to the leading vehicle VR. In this embodiment, guidance by the navigation unit is performed until the vehicle VC reaches a stop road RSTP on which the unable-to-drive vehicle VE stops, the driver of the vehicle VC is advised by the navigation unit that the vehicle VC should become the leading vehicle VR, and after the time the vehicle VC reaches the stop road RSTP, the autonomous and automatic driving of the vehicle VC as the leading vehicle VR is performed to the joining point PJN. This embodiment is the same as the first embodiment except the points described below.

Figure 6A:
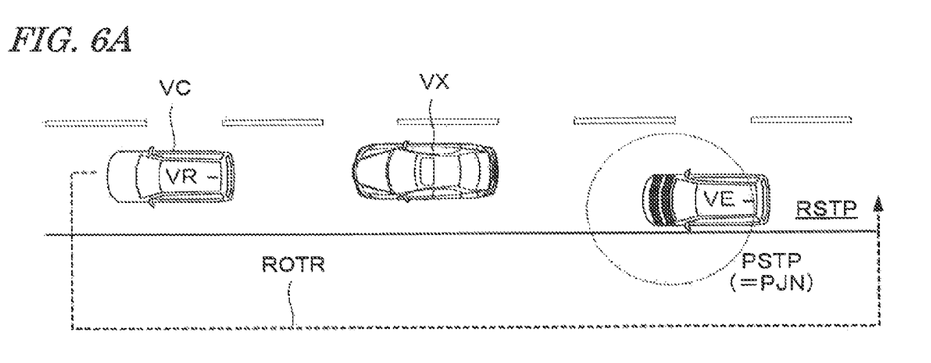
FIGS. 6A, 6B, 7A, and 7B are drawings for illustrating a control upon occurrence of the emergency (second embodiment)
Figure 6B:
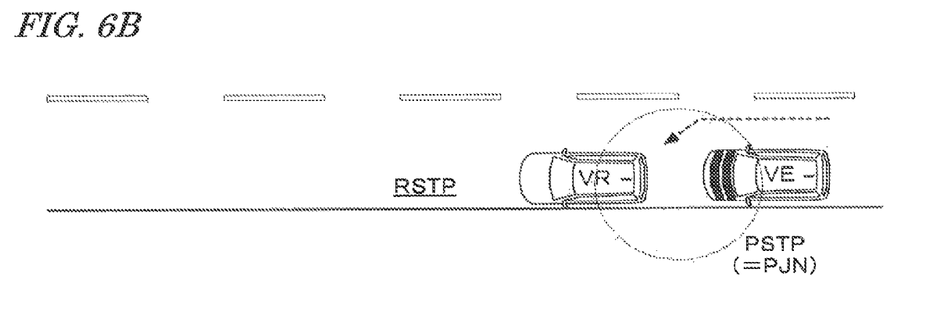

Referring FIGS. 6A, 6B, 7A, and 7B, an outline of the control for coping with the emergency in this embodiment is described below. FIGS. 6A and 6B, similarly to FIGS. 3A-3C, show an example where the vehicle VC runs ahead of the unable-to-drive vehicle VE. If the unable-to-drive state of the driver is detected or determined, the unable-to-drive vehicle VE promptly stops (at a stop position PSTP), as shown in FIG. 6A. The road on which the unable-to-drive vehicle VE stops is referred to as "stop road RSTP". In this example, the vehicle VC runs ahead of the unable-to-drive vehicle VE. However, the vehicle VC cannot join the unable-to-drive vehicle VE if the vehicle VC stops on the stop road RSTP and waits for the vehicle VE.

Accordingly, the driver of the leading vehicle VR (VC) is advised using the route guidance function of the navigation unit 32 so that the leading vehicle VR runs out of the stop road RSTP and returns through another route ROTR to the stop road RSTP at a position behind the stop position PSTP (right end in FIG. 6A). When the leading vehicle VR returns to the stop road RSTP with the driving by the driver according to the guidance of the navigation unit 32, the autonomous and automatic driving is started, wherein as shown in FIG. 6B, the leading vehicle VR stops immediately ahead of the unable-to-drive vehicle VE, and the convoy lead driving is begun. The control thereafter is the same as that in the first embodiment. As described above, in this example, the driver of the leading vehicle VR drives the leading vehicle VR according to the guidance from the time the vehicle VR runs out of the stop road RSTP to the time the vehicle VR returns to the stop road RSTP, and the autonomous and automatic driving is started from the time the vehicle VR returns to the stop road RSTP.

Figure 7A:
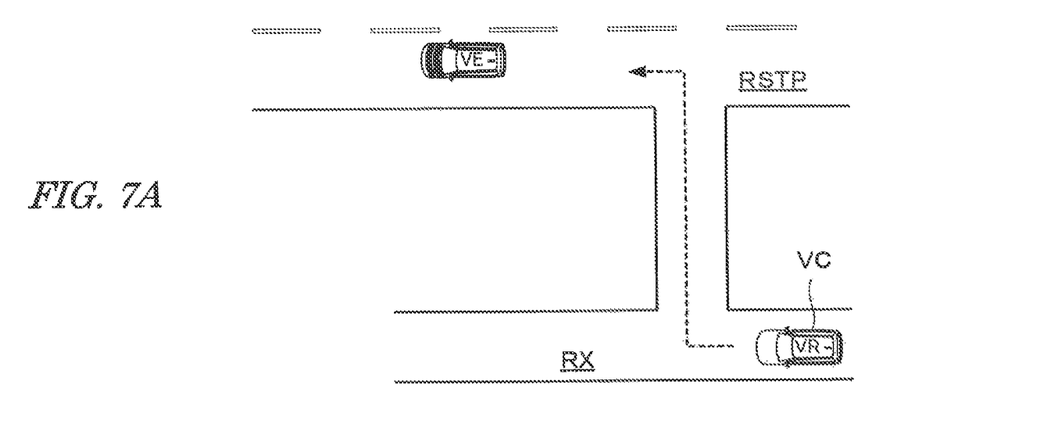
Figure 7B:
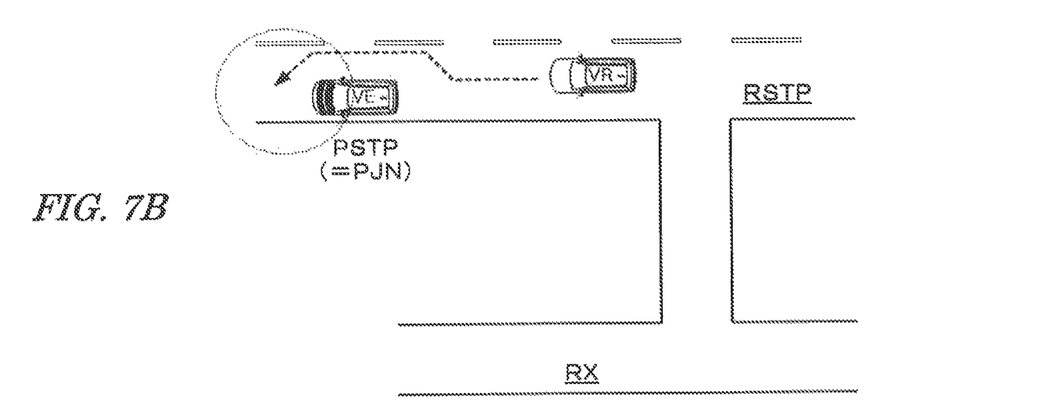

FIGS. 7A and 7B show an example wherein the vehicle VC receives the emergency information to become the leading vehicle VR when the vehicle VC runs on another road RX which is different from the stop road RSTP. In this example, the driver drives the vehicle VC according to the route guidance of the navigation unit 32 from the other road RX to the stop road RSTP, and the autonomous and automatic driving is performed from the time the vehicle VC reaches the stop road RSTP until the vehicle VC (VR) reaches the stop position PSTP (=the joining point PJN).

Figure 8:
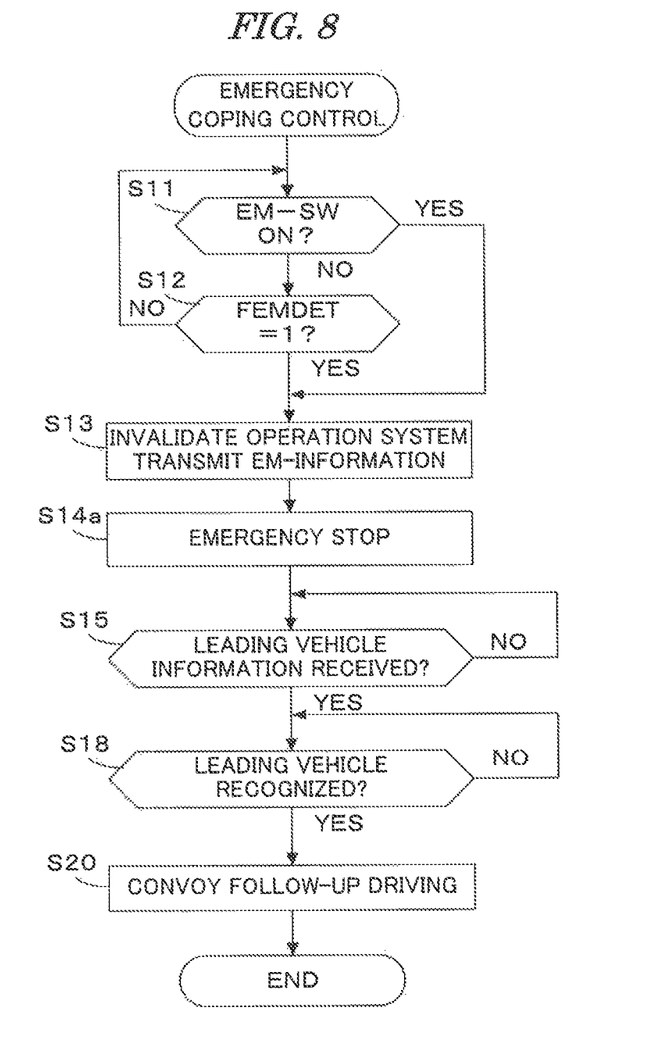
FIG. 8 is a flowchart of a control for coping with the emergency, the control being performed when the driver of the present vehicle has become the unable-to-drive state (second embodiment)

FIG. 8 is a flowchart of the emergency coping control in this embodiment (the control performed when the vehicle 1 has become the unable-to-drive vehicle VE). This control process is obtained by deleting steps S16, S17, and S19 of FIG. 4 and replacing step S14 with step S14a.

In step S14a, the vehicle 1 (unable-to-drive vehicle VE) is promptly stopped, and the leading vehicle information is received (step S15). If the leading vehicle VR stopped just in front of the vehicle 1 is recognized (step S18), the convoy follow-up driving is started (step S20).

Figure 9:
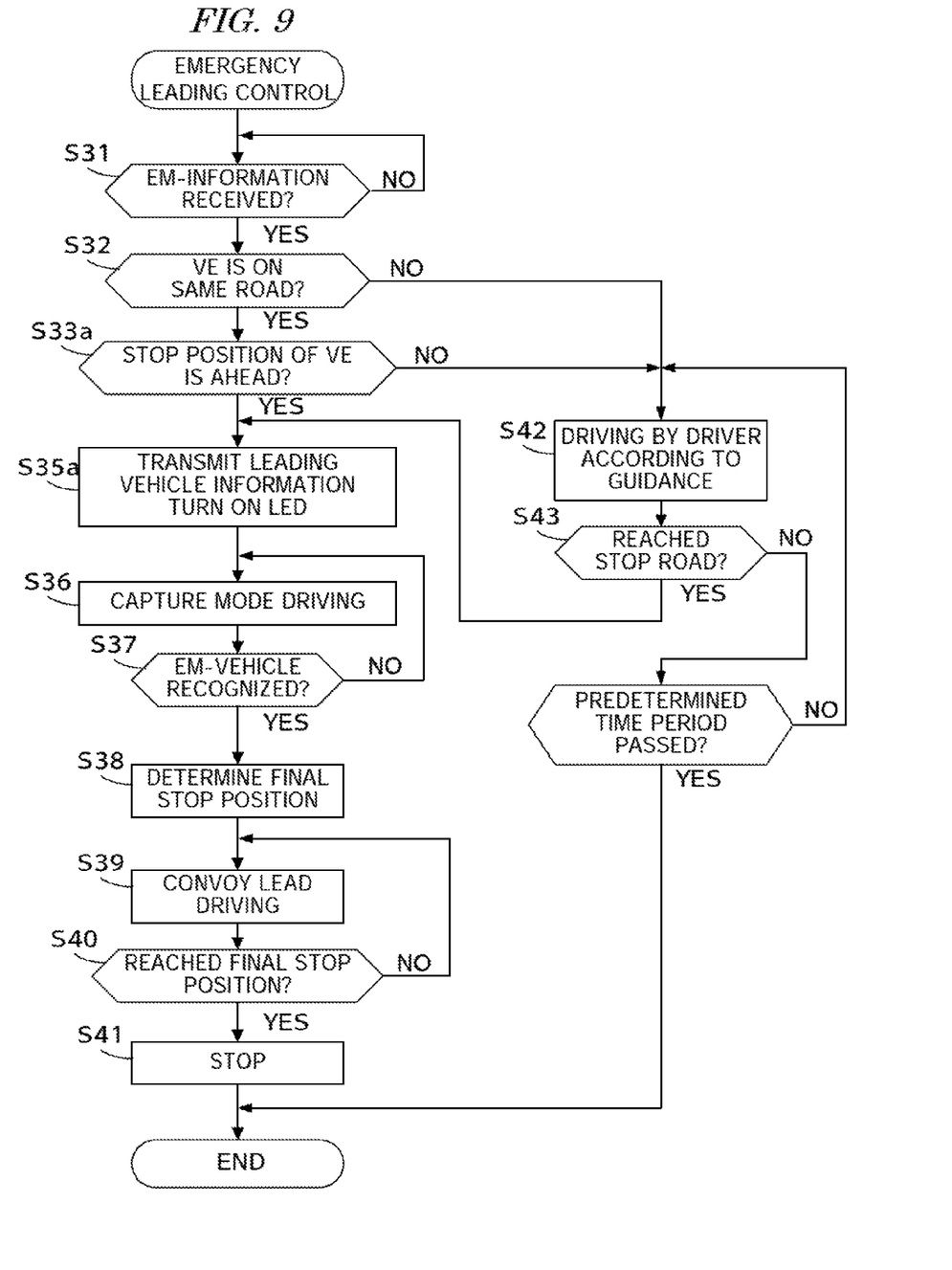
FIG. 9 is a flowchart of an emergency leading control which is performed when the present vehicle corresponds to a vehicle which should lead the unable-to-drive vehicle (second embodiment).

FIG. 9 is a flowchart of the emergency lead control in this embodiment (the control performed when the vehicle 1 has become the leading vehicle VR). This control process is obtained by replacing steps S33 and S35 of FIG. 5 with steps S33a and S35a, and adding steps S42 and S43.

In step S33a, it is determined whether or not the stop position PSTP of the unable-to-drive vehicle VE is positioned ahead of the present position of the vehicle 1. If the answer to step S33a is affirmative (YES), the leading vehicle information (including no information regarding the joining point PJN) is transmitted, and the LED display 41 is turned on (step S35a). Next, the capture mode driving is started (step S36).

If the answer to step S32 or S33a is negative (NO), in other words, the unable-to-drive vehicle VE is stopped on anther road, or at a place on the same road behind the vehicle 1 in the running direction, the guidance with the navigation unit 32 is performed to advise the driver of performing the lead driving (step S42). In step S43, it is determined whether or not the vehicle 1 has reached the stop road RSTP, and if reached, the process proceeds to step 35a.

It is to be noted that the process ends if the condition that the answer to step S43 is negative (NO) continues for a predetermined time period.

As described above, in this embodiment, the unable-to-drive vehicle VE is promptly stopped, which makes it possible to enhance safety of the driver or other vehicles. Further, the driver of the leading vehicle VR is made to drive the leading vehicle VR to the stop road RSTP using the guidance function of the navigation unit 32. Accordingly, it is possible to capture the unable-to-drive vehicle VE and to lead the vehicle VE to the final stop position PDST, even when the stop position PSTP of the unable-to-drive vehicle VE is positioned on the same road behind the leading vehicle VR, or when the leading vehicle VR runs on a road which is different from the stop road RSTP.

The present invention is not limited to the embodiments described above, and various modifications may be made. For example, in the above-described embodiment, the unable-to-drive state of the driver is determined based on the image of the driver obtained by the camera 13. The determination method is not limited to such an indirect method. The driver's state may directly be detected by a sensor (a pulse sensor, a heart beat sensor, etc.) mounted on the steering wheel, the driver's seat, or the like, and the unable-to-drive state may be determined according to the detection result by the sensor.

Further, in the above-described embodiment, the vehicle VE or VR that first reaches the joining point PJN (first-reached vehicle) stops and waits for the other vehicle VR or VE. It may not be necessary for the first-reached vehicle to stop, but the first-reached vehicle may wait for the other vehicle with slow running. For example, when the leading vehicle VR is waiting with slow running, and the unable-to-drive vehicle VE approaches and joins the leading vehicle VR from behind, both of the vehicles may promptly start the convoy running without stopping.

Further, in the above-described embodiment, driving of the leading vehicle VR to the joining point PJN and from the joining point PJN to the final stop position PDST is performed with the autonomous and automatic driving as long as possible. The driver of the leading vehicle VR may perform the whole driving without using the autonomous and automatic driving.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A control apparatus of a leading vehicle comprising:
   unable-to-drive vehicle recognizing means for recognizing an unable-to-drive vehicle of which a driver thereof has come into an unable-to-drive state where the driver is unable to drive the unable-to-drive vehicle;
   lead running control means for performing a lead running control for making said unable-to-drive vehicle follow said leading vehicle;
   joining point obtaining means for determining a joining point at which said leading vehicle is to join said unable-to-drive vehicle;
   automatic joining driving means for autonomously and automatically driving said leading vehicle to the joining point such that the unable-to-drive vehicle joins thereto; and
   final stop position obtaining means for obtaining a final stop position near a medical institution,
   wherein said lead running control means controls said unable-to-drive vehicle to follow the leading vehicle to the final stop position by autonomous and automatic driving.

2. The control apparatus according to claim 1, further comprising invalidating means for invalidating an operation system which is normally operable by the driver of said unable-to-drive vehicle.

3. The control apparatus according to claim 1, wherein said control apparatus promptly stops said unable-to-drive vehicle when the unable-to-drive state of the driver is detected or determined, and the joining point obtaining means obtains a stop position of said unable-to-drive vehicle as the joining point.

4. A control method for first and second vehicles, comprising the steps of:
   a) detecting or determining, in said first vehicle, an unable-to-drive state of the driver of said first vehicle, the unable-to-drive state being a state where the driver is unable to drive said first vehicle;

b) sending outside notification from said first vehicle of the detection/determination result when it is detected or determined that the driver of the first vehicle has come into the unable-to-drive state;

c) recognizing, in said second vehicle, based on the notification sent in said step b) that the driver of said first vehicle has come into the unable-to-drive state;

d) obtaining, in said first vehicle, a joining point at which said first vehicle is to join said second vehicle;

e) obtaining, in said second vehicle, the joining point at which said second vehicle is to join said first vehicle;

f) performing, in said first and second vehicles, autonomous and automatic driving of said first and second vehicles to the joining point;

g) recognizing, in said first vehicle, said second vehicle at the joining point;

h) recognizing, in said second vehicle, said first vehicle at the joining point; and i) performing, in said first vehicle, a follow-up running control for making said first vehicle automatically follow said second vehicle, and performing, in said second vehicle, a lead running control for leading said first vehicle to a final stop position near a medical institution.

5. The control method according to claim 4, further comprising the step of invalidating an operation system which is normally operable by the driver of said first vehicle.

6. The control method according to claim 4, further comprising the step of promptly stopping said first vehicle when the unable-to-drive state of the driver of said first vehicle is detected or determined, and a stop position of said first vehicle is determined as the joining point.

* * * * *